United States Patent
Lambalk et al.

(10) Patent No.: US 6,903,249 B2
(45) Date of Patent: Jun. 7, 2005

(54) LETTUCE PLANTS HAVING BROAD-SPECTRUM DM-RESISTANCE GENES

(75) Inventors: Johannes Jacobus Maria Lambalk, Middenbeemster (NL); Nanne Machiel Faber, Hoorn (NL); Arie Bastiaan Bruijnis, Hoorn (NL); Petrus Cornelis Johannes Conijn, Noordbeemster (NL); Ijfke Arendtje Dèn Witte, Enkhuizen (NL); Jacqueline Nieuwenhuis, Oostzaan (NL); Cornelis Jacob De Jong, Enkhuizen (NL)

(73) Assignee: Enza Zaden, de Enkhuizer Zaadhandel B.V. (NL)

(*) Notice: Subject to any disclaimer, the term of this patent is extended or adjusted under 35 U.S.C. 154(b) by 0 days.

(21) Appl. No.: 09/959,037
(22) PCT Filed: Apr. 13, 2000
(86) PCT No.: PCT/NL00/00241
§ 371 (c)(1), (2), (4) Date: Mar. 8, 2002
(87) PCT Pub. No.: WO00/63432
PCT Pub. Date: Oct. 26, 2000

(65) Prior Publication Data
US 2004/0226060 A1 Nov. 11, 2004

(30) Foreign Application Priority Data
Apr. 16, 1999 (NL) .............................. 1011819

(51) Int. Cl.⁷ ............................ A01H 1/00; A01H 5/00; A01H 5/10
(52) U.S. Cl. ..................... 800/305; 800/269; 800/298
(58) Field of Search .............................. 800/298, 266, 800/267, 269, 305

(56) References Cited

PUBLICATIONS

Bonnier et al 1992, Euphytica 61: 203–211.*
Dufresne et al 2004, Nature Biotechnology 22(2): 231–232.*
Farrara et al 1987, Plant Pathology 36: 499–514.*
Maisonneuve et al 1994, Theor. Appl. Genet. 89: 96–104.*
Kessell, Rick et al., "Recessive Resistance to *Plasmopara lactucae–radicis* Maps by Bulked Segregant Analysis to a Cluster of Dominant Disease Resistance Genes in Lettuce," *Molecular Plant–Microbe Interactions*, vol. 6, No. 6, pp. 722–728, 1993.
Michelmore, R.W. et al., "Molecular Markers and Genome Analysis in the Manipulation of Lettuce Downy Mildew," *Advances in Molecular Genetics of Plant–Microbe Interactions*, pp. 517–523, 1993.
Paran, I. et al., "Development of reliable PCR–based markers linked to downy mildew resistance genes in lettuce," *Theory of Applied Genetics*, vol. 85, pp. 985–993, 1993.
Paran, I. et al., "Identification of restriction fragment length polymorphism and random amplified polymorphic DNA markers linked to downy mildew resistance genes in lettuce, using near–isogenic lines," *Genome*, vol. 34, pp. 1021–1027, 1991.
Farrara, Barry F. et al., "Identification of New Sources of Resistance to Downy Mildew in *Lactuca* Spp.," *HortScience*, vol. 22, No. 4, pp. 647–649, 1987.
Farrara, B. et al. "Genetic analysis of factors for resistance to downy mildew (*Bremia lactucae*) in species of lettuce (*Lactuca sativa* and *L. serriola*)" *Plant Pathology* 36: 499–514 (1987).
Landry, B. et al. "A Genetic Map of Lettuce (*Lactuca sativa* L.) With Restriction Fragment Length Polymorphism, Isozyme, Disease Resistance and Morphological Markers" *Genetics* 116: 331–337 (1987).
Maisonneuve, B. "Utilisation de la culture in vitro d'embryons immatures pour les croisements interspécifiques entre *Lactuca sativa L*. et *L. saligna L*. ou *L. virosa L.*; étude des hybrides obtenus ("Interspecific hybridization in *Lactuca* sp. using in vitro culture of immature embryos, and study of hybrid offspring")" *Agronomie* 7(5): 313–319 (1987) (The summary is in English).
Maisonneuve, B. et al. "Rapid mapping of two genes for resistance to downy mildew from *Lactuca serriola* to existing clusters of resistance genes" *Theor Appl Genet* 89: 96–104 (1994).
Michelmore, R., et al. Clusters of Resistance Genes in Plants Evolve by Divergent Selection and a Birth–and–Death Process: *Genome Research*8: 1113–1130 (1998).
Stam, P "Construction of integrated genetic linkage maps by means of a new computer package: JoinMap" *The Plant Journal* 3(5): 739–744 (1993).
Williams, J., et al. "DNA polymorphisms amplified by arbitrary primers are useful as genetic markers" *Nucleic Acids Research* 18(22): 6531–6535 (1990).
Michelmore, R. et al. The inheritance of virulence in *Bremia lactucae* to match resistance factors 3, 4, 5, 6, 8, 9, 10 and 11 in lettuce (*Lactuca sativa*) *Plant Pathology* 33: 301–315 (1984).

* cited by examiner

*Primary Examiner*—David H Kruse
(74) *Attorney, Agent, or Firm*—Webb Ziesenheim Logsdon Orkin & Hanson, P.C.

(57) ABSTRACT

A method for obtaining a plant, in particular a cultivated lettuce plant (*L. sativa*), with a lasting resistance to a pathogen, in particular *Bremia lactucae*, comprising of providing one or more specific DNA markers linked to one or more resistance genes, determining the presence of one or more resistance genes in a plant using these DNA markers, subsequently crossing a first plant comprising one or more resistance genes with a second plant comprising one or more resistance genes, and selecting from the progeny a plant in which one or more resistance genes are present by using the DNA markers. The invention further relates to the plants obtained with this method, seeds and progeny of these plants, as well as progeny thereof.

6 Claims, 7 Drawing Sheets

CCGCAGTCTGAGTTGAGCAATCGATGGATAGTTGAGTCGTTACTTTTTGT
GGCAAGAGTTGCATTGTTCCCGTTCCTGGGAAAAGCGAAGTAACTATCGA
AATTCCGGTTTCAAAGTTTGGAGGTAGGCTCCGTAGGGTAGCATTGATGG
TGACCCTTTTCATCAGAGTATTTGGGCAGTTTGTATGCTGTAAGGTATTT
TCTTTTACCATGGAGTCATTGGTGGAGGATGAGATGGAAGAGATCCATGA
AGGTGCCTTTTGAGGATGGCATGCATTTAGCAGCGGTTTCAGGTAGTAAG
AGGAATATATCAGGGCGGTGGCCCTCATAGTTAGGATTGTGCATCGGTTA
TGAGAGTGAGACCTTGTGTCTTGATGATGATTCCCGTGTTGGGAGGCGGG
TCGATGAATCAAAGACGAGGGGTGTGATAGTGTATTATTTCCAGACTGCG
G

FIG.1

CAGACCGACCCAACCCTTTCGACTTCCGATTTCTAACGGTTCTTTTTATA
AAACATTCCTAAATTACCATACTAACAAAATAACATTTCCATTTATCTTA
AGCCCCTTAACTTTTGTTTTTTACTTTAACCTGCCTTTTTTCTTTTTAA
TTTTTATTACAAATTTAGTCTAAACTTATTTTTTTACAACTTTCTTTTT
ATATAATTTCTAAAATTTAGGCTTTTAAAAAAATTATTTGTTACAATT
TTATAAAATTTGATTTTTACAAATATTCTTTTAATTTTGTTTATATTT
TCTTTTCTTAGATTTTTCTGATTTTATAAATTATATTTTTTAATTAGTT
TTCTATATTCTACAAAAATTATTTTTTACATAATTTTTTTTTCAAATTGT
TTTTAAAAAACTAATATTCTTTAGAAAATTATTTTTACAAAGAGTTATAT
ATTTGGTTTTATGCATGTATTTAAAAAAATTCCCGCATTTAAATAAATA
TTATTCTTTAAAATTTATTTACTATTTTTATATATTCATTTACATGGTCG
GTCTG

CCAGCAGCTTGCCAAACAAAGGCTAAAAAAAGAAAAAAGAACAGGGGTATGACTGGCATAACATCTAC
GATTGGATTCAAAAAAGCATAGGCTTCGGGCAATTTAGCGAAGAAAAGACTACTGGATAAAGGG
TAGAATTAAGACAGATCAAAGTAAAGATAATATGCATAACATACATTTGTTCGTCGAGATAATT
GCATTTGATTGAGTTAGGAAGAGAATTCAATGTTTGAAGAATGAATTGTCTAAAACAATTGTTG
GATTCGAAGCTGCTGG

FIG. 4

GACAGTCCCTTCACTAGTACTTGCTTTACTAAAACAACAACTATAATCCATCTTAATTTCCTT
CTACGTACAGATTAATAAGCAAAATGAACTTTTTGGCAACTTAAATTCGAGTCCCTAC
ACTAGTACTTGATAGATCTACTTTCATTTCTCCACCCCATGTGGTCATCGCTTGTTAAGGT
GACATATAAACCACTCTCTAAGTCATCCTCTAATGTCATCACCTAAGAGGCTTATTCTTC
CTCTTTTCCAGTAAACATAAACAAGAACATGTGATATAATGAAACAAAATAGAAATTCAACTG
TTAAAAGAATTGATTCTGTAACACCCCTGTTTATTTATTAGATATAAATTAATTACTGAACAA
ATGGTAGCCCTAAATAATTATATCAAAGGATGGTCTCGAGAACTAATTGTCACAAGT
TTCCAAGTTGGGGTTAAAGTGTGACTTCATTTGTAAATAAATTTGTGGAGGCAAGGA
CTAAATAGTAAATTATTGACTTCATTTGAAATAAATGTAGGAGGGGCTACTTGGTAAAAGT
TGGACTTAATTAGTAAGGGGATTAAGAGGCAGGGTTCAACTGGTACCTTATGGGTTCACTTTGAA
AGAAGAATGGTATGGGAGGGACTGTC

FIG. 5

```
GGGAGAGGGAGATACTATGTTTCTCGCGTATCAAAGATTACTCCGTTAAGGGTAATATTAA
TCCCAGTACTTCTCGTCAAGTCAACTTAAACACTTGTACCACAGCGTTAGGAAAAATCGAACG
AACCTTGTTACTATCCTCCAAAGAAAAACCAAAAACCCCTCCTTATTTCACGAGCATACCAACA
ATCTATTCCCCAACTTTCCCCAGCTTTCCTACGATGTTGACACTACATATTGAACAAGAACATA
AGTACTACAATCCATTCTGTCGCGCCGTAACAATGCCTAAGTGCCAAGTAGAACCTCTTG
GTAAAAACAGAACCCTGAAGGACTAATATAACTAGCGAAGAGGTTAGGAAGTACTAGTGACGCTA
TCCGACTTTTATAGTTAGTAATTTGTGAATATTTCCTATTAATGGGTGATCTTCTAATTGA
AACTATCTGTAGTATTTGCGACTGGCGTTTACAATTAAGATTTTTCAATTAAGCCTTAAACTAAC
AACTATACTTTTARAACTACATATARTTATTKCCCTTACCGAAGCCTTATTCCGTGTAGTTTTAA
AAGAAGTATCTTTGTAGTTATAGTTGCTACATATGTTCAAGTTCCAGAGATTTAGCTGGTGTAT
TGTGTTTGTTAAGTTCGTCAAATTCCAATATGTTACCCCTACCCATATGTTGAATTGATATGAGTGG
TTAAAGAAATCTCTGAAAGACTCGGGACCTTTAAGTCAAGGAGGAGTTGCGTTCAAAACAGTA
GGGACATNTAAATCCTTAAATGTGAACTCCACCGCGTTGATGGGAAAAAAATCCAGACCTCCAATGTACTTTG
TTCCCTTTAGATTATTTTACTTTTCTCGACTTTACCTAAATATTCATTAGTAGTTGTTCGATGTAGATTC
ATATTATATGTACAAACGATTGTTCAACAGAATATATTTTTACTACTCCATCTATTGTTAATCTTTCACTGTC
GCTTTTCTTTGACGTTATTGCTTAAATGTTTTTACTTAAGTTATTAGTAGTCCATCTATTGTTAATCTTTCACTGTC
TCATATGAAACTTCTATTCCCTTAAGTTCTCCCCTCTCCC
```

FIG.6

```
CAAAGCGCTCCATCTTGTAGGATTCTTTATTGGTAGGAAATGGGCGGATTTCGTTAGTCTATCA
ACTATTACCCAGATTGTGTCCAAACTGTCTGGGCACTTGGGTAGTTTGATCACGAAATCCATGGT
AATCCTTTCCCATTCCACTCGGAATTACTAGCTGTGTAGTAATCCAGAGGGCTTCTGATATT
TAACCTTTACTTTAGCACAAGTGAGGCACTTGCTTACGTAAGTGTAATCTCTGCCCTTCATATTTG
GCCACCAATAATGCTGCTTAACATCTAAGTACATCTTGTCTGAACCCGGATGGAGTATCGC
GTCTTGTGAGCCTCGTTCATGAATACCCTCTCCACCTCCAAGTTTAGGACCAATATGCGGTT
CATGAAGTAGTATGTTCCATCTTCCTTCACCTCCAAGTTCTCTCCATTCCACGCAGGCCTTCAC
TCGTTTGTTCTCCGCCTTCATCGAGAGAGTTTCATACAAAGACTTGAGTATTCTTTCTGACTCAAGGCATCGGC
TGGATGGTTATCGAGAGAGTTTCATACAAAGACTTGAGTATTCTTTCTGACTCAAGGCATCGGC
TACCACGTTAGCCTTGCCTGGATGTACTGATGTCGCACTCATAGTCGTTCAGCAGTTCGACCC
ATCTTCATTGCCCTCATGTTTAGCTCCTTTGATTCAAGATGTGCTGAAGACTCTTGTGTCAGTG
AAGATAGTGCACTTGGTACCGTATAGGTAGTGTCTCCAGATTTCAGGGCGAAGACCACTGCACC
CAGTTCCAGATCGTGGGTCGTATAATTNCTTCGTGTCTTTTAGCTGTCGGGACGCGTAAGCTAT
CACCCTTCCACGCTGCATGAGTACACAGCCTAAACCCTGATTTGACGCATCGCAGTAGACTATAA
AGTCTTCTGTTCCTTCAGTAGTGATAGCACCGGTGCACTGCAGAGCGCTTTG
```

LETTUCE PLANTS HAVING BROAD-SPECTRUM DM-RESISTANCE GENES

BACKGROUND OF THE INVENTION

1. Field of the Invention

The present invention relates to a method for obtaining a plant with a lasting resistance to a pathogen. The invention also relates to a plant in which two or more resistance genes to the pathogen are present, in addition to seeds and progeny of this plant, and progeny thereof.

The invention relates particularly to a method for obtaining a cultivated lettuce plant (*L. sativa*) with a lasting resistance to *Bremia lactucae*. The invention also relates to DNA-markers which are specifically linked to a resistance gene to *Bremia lactucae*. The invention further relates to a cultivated lettuce plant (*L. sativa*) in which two or more Dm-resistance genes are present, and to seeds and progeny of this plant, and progeny thereof.

2. Description of the Related Art

The disease which is caused by the fungus *Bremia lactucae* Regel is known as downy mildew. Downy mildew occurs worldwide and represents a great problem for both the yield and quality of cultivated lettuce. The fungus can infect the lettuce plant at any stage of growth, after which the first symptoms of downy mildew consist of the appearance of chlorotic yellow spots on the leaf surface. Within 24 to 48 hours a white fluffy fungus growth then becomes visible an the lower leaf surface as an indication of spore formation. During the infection the lesions become increasingly larger and more chlorotic until the leaves become completely brown.

*Bremia lactucae* is one of the so-called Oomycetes, a class of relatively primitive fungi. Other known fungi of this group are for instance *Phytium* and *Phytophtora*. The fungus *B. lactucae* contains different physiological species ("physios") and is host-specific. *Bremia lactucae* is known as a very variable pathogen. New physios occur relatively frequently through mutation of the avirulence genes during the spore formation preceding the propagation of *B. lactucae*.

Within the *Lactucae* genus, to which the cultivated lettuce (*Lactuca sativa*) belongs, there are different species which are resistant to *Bremia lactucae* Regel. The resistance is based in most cases on qualitative genes, known as Dm-resistance genes (Dm=Downy mildew). The resistance mechanism is known as a gene-for-gene working principle based on the specific interaction between products of the Dm-resistance gene and the pathogen-specific avirulence gene, which results in resistance of the lettuce plant (Michelmore et al., Plant Pathology 33, 301–315, 1984). This resistance mechanism has also been demonstrated for diverse other resistance genes in different other plant species (Michelmore et al., Genome Research, 8, 1113–1130, 1998).

A large number of Dm-resistance genes have already been identified which can bring about resistance to specific physics of *Bremia lactucae* Regel. Genetic research has shown that these Dm-resistance genes often occur clustered in groups on the same chromosome. Four such linking groups on different chromosomes in the genome of lettuce have been demonstrated which contain different Dm-resistance genes (Farrara et al., Plant Pathology 36, 499–514, 1987). Newly identified Dm-genes can often be classified into one of the known resistance linking groups.

A major problem however is that *Bremia lactucae* physics continue to occur which "break down" the resistance resulting from the known Dm-resistance genes in the present cultivated lettuce varieties. This implies that *Bremia lactucae* physios occur to which there is no resistance in present cultivated lettuce varieties. Resistance genes can however sometimes still found in old lettuce cultivars, but particularly in wild *Lactucae* species related to cultivated lettuce, such as for instance *L. virosa* and *L. serriola*. A number of broad-spectrum Dm-resistance genes have been identified with a resistance to all tested *Bremia* physios.

Dm-resistance genes from old lettuce cultivars or from wild lettuce species can be crossed into cultivated lettuce to once again obtain resistance. Crossed-in Dm-resistance genes have been demonstrated in conventional manner by means of an artificial *Bremia lactucae* disease test. For this purpose a number of leaf punches—(diameter 18–20 mm) or seedlings of the lettuce plant are inoculated with different physios of *B. lactucae*. After 10 to 14 days the degree of development and sporulation on the punches/seedlings is then examined. On the basis hereof it is possible to judge whether a tested lettuce plant or improved line is resistant or susceptible to the tested *B. lactucae* physios.

When it is known that two or more new Dm-resistance genes occur in different linking groups, these resistance genes can be brought together ('stacked') in a cultivated lettuce plant by crossing-in, thereby reducing the danger of the resistance being broken down. Stacking of a plurality of qualitative broad-spectrum Dm-resistance genes from different linking groups can however not be carried out with the conventional *Bremia lactucae* disease test because, when one qualitative Dm-resistance gene is present, total resistance is already detected in the disease test and the possible presence of a second broad-spectrum Dm-resistance gene will therefore not be detected. It is therefore not possible to select precisely those plants in which two or more qualitative broad-spectrum Dm-resistance genes are present and thus obtain plants with a lasting resistance to *B. lactucae*.

It is therefore desirable for a method to be developed with which, after crossing of qualitative resistance genes into a plant, those plants can be identified and selected in which two or more resistance genes are present.

SUMMARY OF THE INVENTION

The general object of the present invention is therefore to provide a method for obtaining a plant with a lasting resistance to a pathogen. A particular objective of the present invention is to provide a method for obtaining a cultivated lettuce plant (*L.sativa*) with a lasting resistance to *B. lactucae*.

The invention provides for this purpose a method for obtaining a plant with a lasting resistance to a pathogen, comprising of providing one or more specific DNA-markers linked to one or more resistance genes, determining the presence of one or more resistance genes in a plant using these DNA-markers, subsequently crossing a first plant comprising one or more resistance genes with a second plant comprising one or more resistance and selecting from the progeny a plant in which two or more resistance genes are present using the DNA-markers.

The present invention particularly provides a method for obtaining a cultivated lettuce plant (*L. sativa*) with a lasting resistance to *Bremia lactucae*, comprising of providing one or more specific DNA-markers linked to one or more Dm-resistance genes, determining the presence of one or more Dm-resistance genes in a cultivated lettuce plant and/or wild lettuce plant using these DNA-markers, subsequently crossing a cultivated lettuce plant comprising at least one or more Dm-resistance genes with another cultivated lettuce plant or a wild lettuce plant comprising at least one or more Dm-resistance genes, and selecting from the progeny thereof a cultivated lettuce—plant with two or more Dm-resistance genes using the DNA-markers.

With the method according to invention plants, particularly cultivated lettuce plants, can be obtained in simple manner which comprise two or more resistance genes, particularly two or more Dm-resistance genes, with a lasting resistance to a pathogen, particularly *Bremia lactucae*. The selection of plants in which two or more qualitative resistance genes are present can only be accomplished using molecular DNA-markers which can demonstrate the specific genes in the genome of the lettuce plant. With the conventional disease tests it is not possible to demonstrate the presence of two or more qualitative resistance genes in a cultivated lettuce plant. The method according to invention can also be used for quantitative resistance genes.

According to the invention the resistance genes are preferably qualitative resistance genes, and the resistance genes are preferably located in different linking groups.

In order to enable identification and selection of a plant with two or more resistance genes, use is made of specific molecular DNA-markers linked to the resistance genes. Use can be made herefor of different DNA-markers such as for instance RAPD (random amplified polymorphic DNA), AFLP (amplified fragment length polymorphism), SCAR (sequence characterized amplified region) etc. The specific DNA-markers linked to the resistance genes are developed in accordance with per se known techniques (Paran et al., Genome 34, 1021–1027, 1991; Paran et al., TAG 85, 985–993, 1993). The application of such DNA-markers to stack different resistance genes in a plant, in particular to combine different broad-spectrum Dm-resistance genes in a lettuce plant (*L. sativa*), in order to obtain a plant, particularly a cultivated lettuce plant (*L. sativa*), with a lasting resistance to a pathogen, particularly *Bremia lacticae*, has however not previously been described.

According to the present invention DNA-markers have been found for four Dm-resistance genes, particularly qualitative broad-spectrum Dm-resistance genes from the *Lactuca* family. Using these DNA-markers it has been established that the four Dm-resistance genes are located in separate linking groups, whereby stacking of the Dm-resistance genes in cultivated lettuce (*L. sativa*) is possible.

BRIEF DESCRIPTION OF THE DRAWINGS

FIG. 1 is a listing of the sequence of DNA marker A;

FIG. 2 is a listing of the sequence of DNA marker B;

FIG. 3 is a listing of the sequence of DNA marker $C_2$;

FIG. 4 is a listing of the sequence of DNA marker $C_3$;

FIG. 5 is a listing of the sequence of DNA marker $C_4$;

FIG. 6 is a listing of the sequence of DNA marker $D_2$;

DETAILED DESCRIPTION OF THE INVENTION

Figure 7:
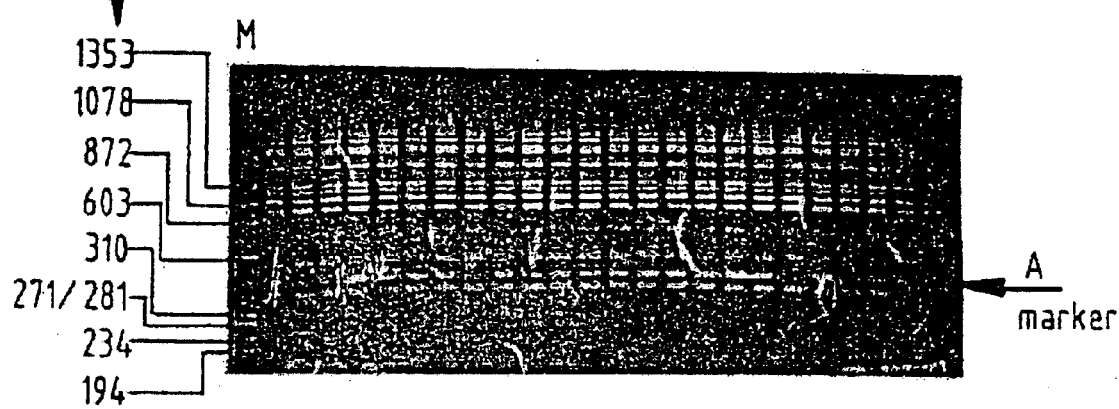
FIG. 7 is a representation of marker analysis of marker A in 24 tested F2 individuals.

There are different methods of demonstrating whether different resistance genes are present in the same or in different linking groups. The position of the DNA-markers can be determined by generating a so-called genetic map or by studying the dependent or independent segregation of the different DNA-markers in relation to each other. In the present invention it was deternined by studying the segregation of the DNA-markers that the specific DNA-markers linked to the Dm-resistance genes segregate independently of each other and are therefore located in four different linking groups.

In the research leading up to the present invention the individuals susceptible and resistant to the same *B. lactucae* phenotype from a population of plants which segregate for *B. lactucae*—resistanre were tested with commercially obtainable RAPD-primers (OPA-01 to OPAN-20, Operon Technologies, Alameda, USA; UBC 1 to 800, University of British Columbia, Vancouver, Canada). RAPD analysis is a per se known technique (Williams at al., Nucleic Acids Research, 18, 6531–6535, 1990) based on the use of primers with a random sequence for the purpose of amplifying random segments of the genomic DNA. Among the amplification products polymorphisms can then be demonstrated on an agarose gel and can be used as genetic markers.

1600 primers (from Operon technologies, and the University of British Columbia, UBC 1 to 800) were used for the study. The DNA of the plants was mixed with the primers in a suitable amplification mixture and subsequently amplified. The amplification products were analysed on an agarose gel for the presence of suitable DNA-markers.

The 'candidate' molecular DNA-markers found in the RAPD-analysis were tested on the individuals of the segregating population, whereafter it was possible to establish which of these DNA-markers were physically linked in suitable manner to the different studied qualitative Dm-resistance genes. In this way the following DNA-markers were identified: DNA-marker A (primer OPAF06, 451 bp); DNA-marker B (primer OPAM10, 555 bp); DNA-marker C1 (primer OPW16, 750 bp), DNA-marker C2 (primer OPL03, 276 bp), DNA-marker C3 (primer OPAE19, 675 bp) and DNA-marker C4 (primer UBC711, 1083 bp); and DNA-marker D1 (primer OPW04, 520 bp) and DNA-marker D2 (primer OPW19, 963 bp). The sequence of the markers A, B, C2, C3, C4 and D2 was then determined and are shown in FIGS. 1–6.

The DNA-markers found were subsequently used to select a cultivated lettuce plant with two or more Dm-resistance genes, after introgression of the resistance genes from wild lettuce species, such as for instance *Lactuca virosa* and *L. serriola*. The crossing into cultivated lettuce varieties of two or more resistance genes, particularly qualitative broad-spectrum Dm-resistance genes, from wild lettuce species, such as for instance *L. virosa*, has not been described previously.

If crossing of two lettuce plants is not successful via the normal methods, use can be made for crossing of the Dm-resistance genes into a cultivated lettuce plant of known cell-biological techniques such as embryo rescue (Maisonneuve, Agronomie 7, 313–319, 1987) or protoplast fusion (Maisonneuve et al., Euphytica 85, 281–285, 1995). In the present invention the different Dm-resistance genes were crossed in as described in Example 2.

Introduction of a new broad-spectrum Dm-resistance gene into one of the four known linking groups can result as a consequence of recombination processes in crossing-out of Dm-resistance genes already present in the linking group, or other resistance genes or horticultural traits with high value. In order to prevent this new qualitative resistance genes with a broad-spectrum Dm-resistance are preferably introgressed into each of the separate linking groups.

The wild lettuce plant used for the method according to invention can for instance be chosen from *L. saligna, L. altaica, L. aculeata, L. homblei, L. indica, L. tenerrima, L. squarrosa, L. viminea, L. augustana, L. quercina*, and *L. cacadensis*. However, other suitable wild lettuce plants can also be used according to the invention. The wild lettuce plant is preferably *L. virosa* or *L. serriola*, more preferably *L. virosa*.

The method according to the invention is preferably used to stack qualitative resistance genes, such as Dm-resistance genes, in cultivated lettuce (*L. sativa*). This further includes for instance head lettuce varieties (*L. sativa Lineaus capitata*), such as iceberg lettuce, batavia lettuce and butterhead lettuce, varieties of leaf lettuce for picking (*L. sativa Lineaus acephala*), such as curly leaf lettuce and stem lettuce, cos lettuce (*L. sativa Lineaus romana*), leaf lettuce for cutting (*L. sativa Lineaus secalina*) and asparagus lettuce (*L. sativa Lineaus angustana*).

The method according to the invention for obtaining a plant with a lasting resistance to a pathogen, as described for cultivated lettuce, can be used in analogous manner for other cultivated crops or other plants, and other pathogens. As non-limitative examples are for instance mentioned obtaining a lasting resistance to determined nematodes, such as *Meloidogyne javanica, M. arenaria*, and *M. incognita*, or to *Oidium lycopersici* in tomato, and obtaining a lasting potyvirus resistance in paprika by crossing-in two or more pvr resistance genes (pvr=potyvirus resistance).

The present invention further provides DNA-markers which are specifically linked to a Dm-resistance gene, and which comprise a DNA-fragment with a sequence which is at least 70%, preferably at least 80%, more preferably at least 90%, and most preferably at least 95% homologous to a sequence as shown in any of the FIGS. 1–6.

The invention further relates to a plant in which two or more resistance genes to a pathogen are present, generally, and particularly to a cultivated lettuce plant (*L. sativa*) in which two or more Dm-resistance genes are present, and to the seeds and progeny of the plant, particularly the cultivated lettuce plant, or the progeny thereof.

A lasting resistance is thus understood to mean in the present invention that there are present in a plant at least two or more resistance genes, for instance two or more broad-spectrum Dm-resistance genes, to a pathogen. The pathogen is for instance *B. lactucae*, but can also be any other organism capable of causing disease in plants, such as for instance fungi, viruses, nematodes, bacteria, (parasitic) insects etc.

In a particularly suitable embodiment of the method according to the invention a Dm-resistance gene is a qualitative, broad-spectrum Dm-resistance gene to the fungus *Bremia lactucae*.

Figure 8:
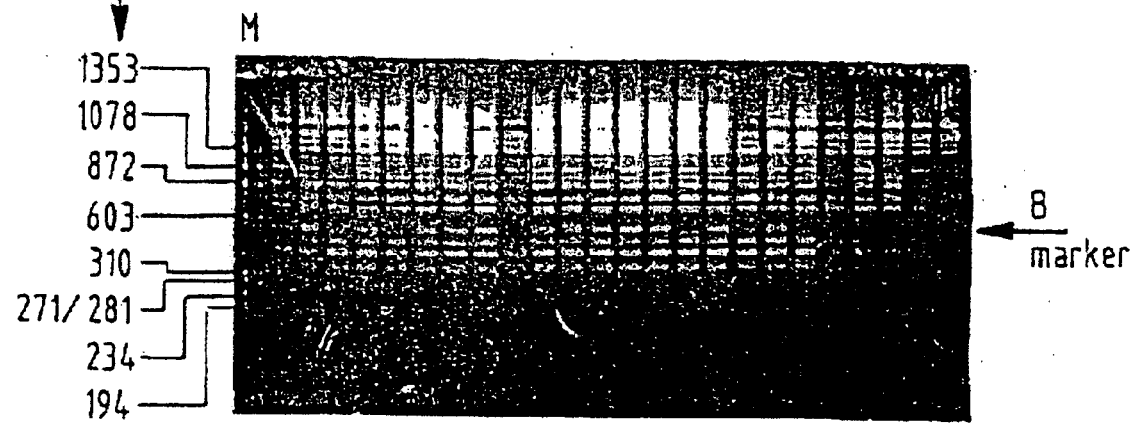
FIG. 8 is a representation of marker analysis of marker B in 24 tested F2 individuals.
Figure 9:
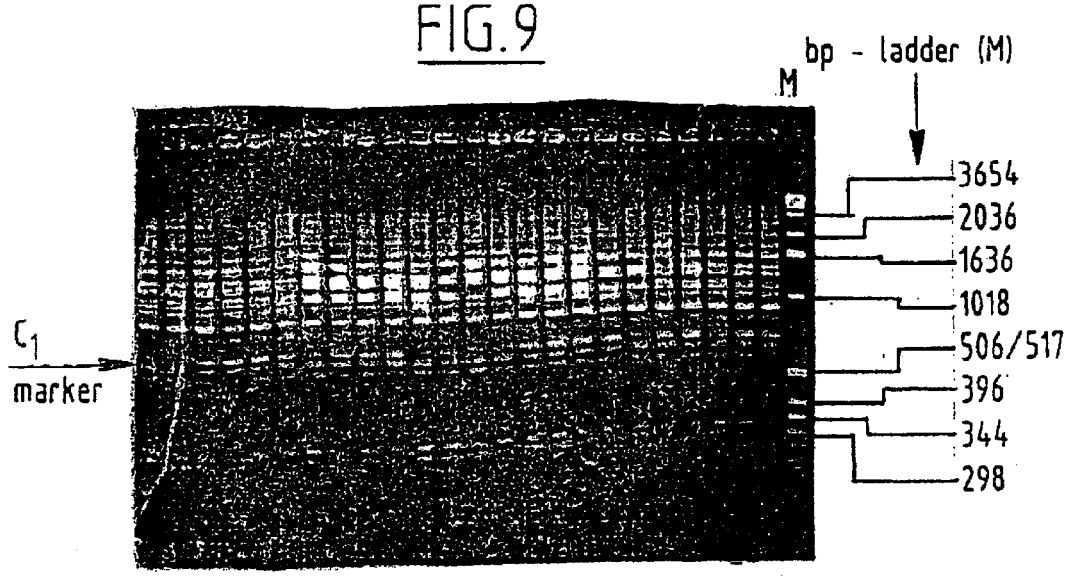
FIG. 9 is a representation of marker analysis of marker $C_1$ in 24 tested F2 individuals.
Figure 13:
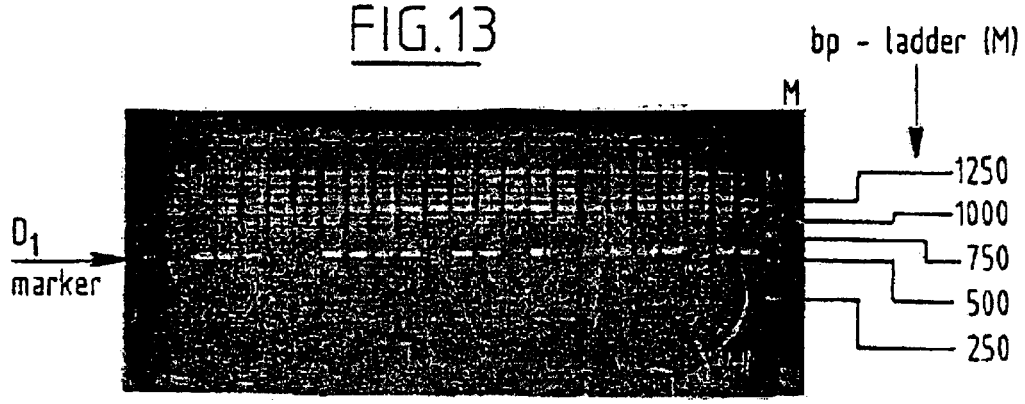
FIG. 13 is a representation of marker analysis of marker $D_1$ in 24 tested F2 individuals.
Figure 14:
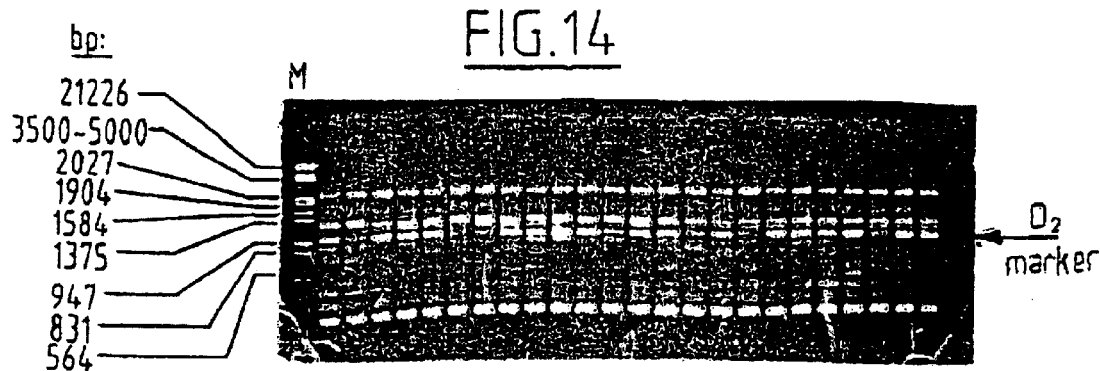
FIG. 14 is a representation of marker analysis of marker $D_2$ in 24 tested F2 individuals.
Figure 10:
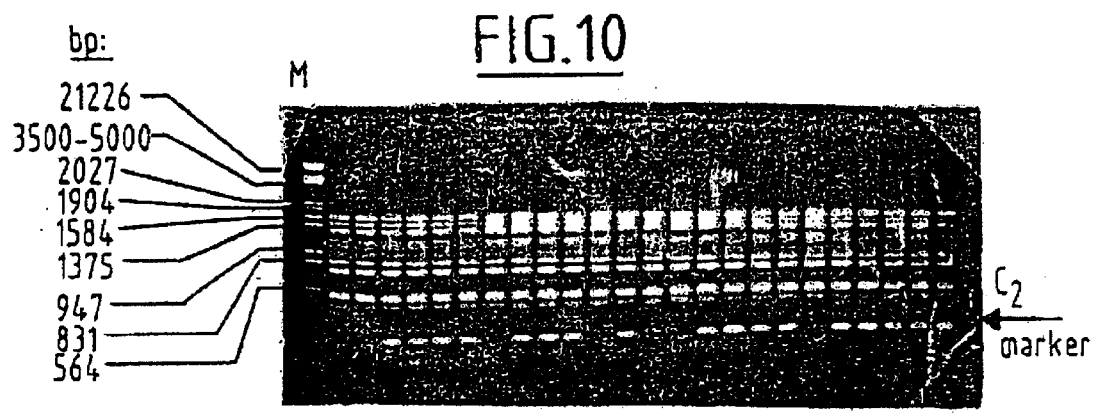
FIG. 10 is a representation of marker analysis of marker $C_2$ in 24 tested F2 individuals.
Figure 11:
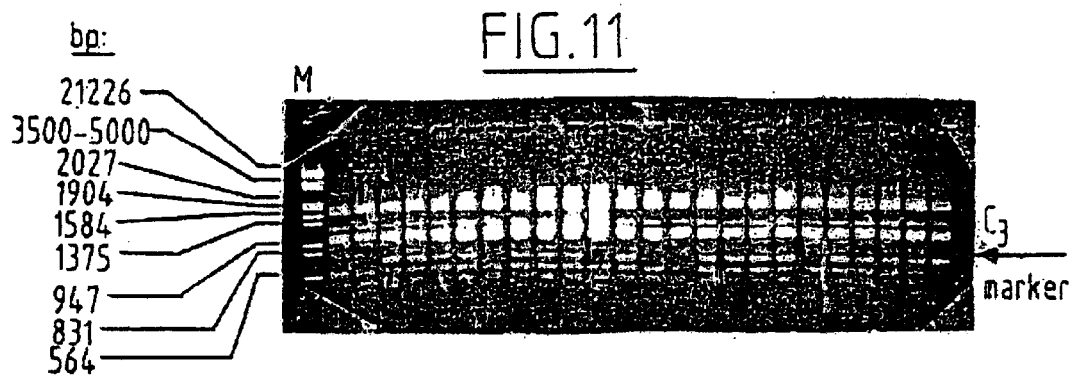
FIG. 11 is a representation of marker analysis of marker $C_3$ in 24 tested F2 individuals.
Figure 12:
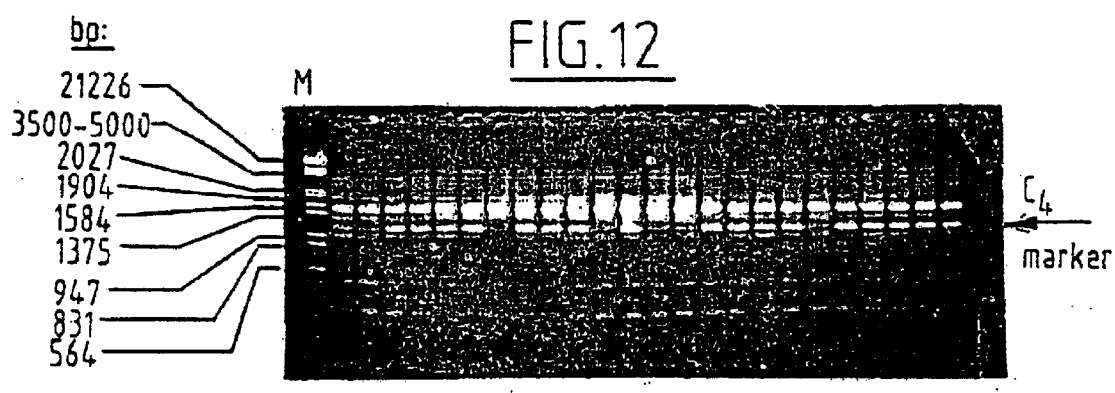
FIG. 12 is a representation of marker analysis of marker $C_4$ in 24 tested F2 individuals.

The invention is described in more detail with reference to the following non-limitative examples and figures, in which:

FIGS. 1–6 show respectively the sequence of the DNA-markers A, B, C2, C3, C4, D2; and FIGS. 7–14 show eight DNA-markers according to the invention in 24 tested F2-individuals. Marker A was identified with primer OPAF06 (451 bp); marker B was identified using primer OPAM10 (555 bp), marker C1 using primer OPW16 (750 bp), marker C2 using primer OPL03 (276 bp), marker C3 using primer OPAE19 (675 bp) and marker C4 using primer UBC711 (1083 bp; DNA-marker D1 was identified with primer OPW04 (520 bp), and marker D2 with primer OPW19 (963 bp).

EXAMPLES

Example 1

Marker Aanalysis in Lettuce F2 Populations which Split for a *Bremia lactucae* Regel Resistance Gene The techniques used to provide fast and directed molecular DNA-markars closely associated with resistance genes to *B.lactucae* are per se known (Paran et al., Genome 34, 1021–1027, 1991; Paran et al., TAG85, 985–993, 1993; Williams et al., Nucleic Acids Research, 18, 6531–6535, 1990), and can be used in analogous manner for identification of DNA-markers in other crops.

From a population (see crossing scheme, example 2) of more than 300 plants which segregate for *B.lactucae* resistance the individuals susceptible and resistant to the same *B.lactucae* phenotype were pooled separately (5 plants per pool). These pools were examined using 1600 commercially obtained RAPD-primers (Operon Technologies, Alameda USA, OPA-01 to OPAN-20; and University or British Columbia UBC 1 to 800). The PCR mixture for the DNA-markers A, B, C1, C2, C3, C4, D1 and D2 was amplified under standard RAPD conditions.

After determining candidate molecular DNA markers using the RAPD-analysis on the DNA-pools, these DNA-markers were checked on individuals of the segregating population, whereafter it was possible to determine which of the DNA-markers were best physically linked to the examined qualitative Dm-resistance gene with a broad-spectrum resistance to *B. lactucae*.

For each of the 4 examined genes with a broad-spectrum Dm-resistance, the best linked molecular DNA-markers are shown in FIGS. 1–6. Marker A was identified with primer OPAF06 (451 bp); marker B was identified using primer OPAM10 (555 bp), marker C1 using primer OPW16 (750 bp). marker C2 using primer OPL03 (276 bp), marker C3 using primer OPAE19 (675 bp) and marker C4 using primer UBC711 (1083 bp); DNA-marker D1 was identified with primer OPW04 (520 bp), and marker D2 with primer OPW19 (963 bp).

Example 2

Crossing Schemes

In this example the crossing schemes for four different populations are shown. The following symbols/characters are used herein:

*=resistant plant, which means: resistance to all tested *B.lactucae* physios.
BC="Back Crossing"
Z=Self-pollinating, the number of figures after Z indicates how many times self-pollination took place.

Population A, *L.virosa* CGN9365, (IVT1398) (marker A)

*L. sativa* X *L. virosa*
(iceberg lettuce type)   CGN9365 (IVT1398)
↓
embryo-rescue
↓
F1 X *L. sativa* (iceberg lettuce type)
↓
embryo-rescue
↓
resistant* BC1 plant X *L. sativa* (iceberg lettuce type)
↓
embryo-rescue
↓
resistant* BC2 plant X *L. sativa* (iceberg lettuce type)
(fertile)
↓
resistant* BC3 plant self-pollination The BC3Z population was then tested and marker A identified. Individual BC3Z plants were self-pollinated and from the BC3Z2 populations the individual BC3Z2 plants homozygous for gene A were selected. The selected plant was used for linking analysis of the diverse identified DNA-markers (Example 3).

Population B, *L.virosa* CGN4683, (IVT280) (Marker B)

*L. sativa* (butterhead lettuce type) X *L. virosa* CGN4683 (IVT280)
↓
embryo-rescue
↓
F1 X *L. sativa* (butterhead lettuce type)
↓
embryo-rescue
↓
resistant* BC1 plant X *L. sativa* (butterhead lettuce type)
(fertile)
↓
resistant* BC2 plant X *L. sativa* (butterhead lettuce type)
↓
resistant* BC3 plant self-pollination The BC3Z population was tested and marker B identified. Individual BC3Z plants were self-pollinated and from the obtained BC3Z2 populations the individual BC3Z2 plants homozygous for gene B were selected and used for linking analysis of the diverse identified DNA-markers (Example 3).

Population C, *L.virosa* CGN5148 (IVT1538) (Marker C1, C2, C3 and C4)

*L. sativa* X *L. virosa*
(butterhead lettuce type) CGN5148 (IVT1583)
↓
embryo-rescue
↓
F1 X *L.sativa* (butterhead lattuce type)
↓
embryo-rescue
↓
resistant* BC1 plant X *L. sativa* (butterhead lettuce type)
(fertile)
↓
resistant* BC2 plant X *L. sativa* (butterhead lettuce type)
↓
resistant* BC3 plant self-pollination The BC3Z population was tested and markers C1, C2, C3 and C4 identified. The individual BC3Z plants were self-pollinated and from the BC3Z2 populations the individual BC3Z2 plants homozygous for gene C were selected and used for linking analysis of the diverse identified DNA-markers (Example 3).

Population D, *L.serriola* CGN5913 (IVT1308) (Marker D1 and D2)

*L. sativa* (butterhead lettuce type) X *L. serriola* CGN5913 (IVT 1308)
↓
F1 X *L. sativa* (butterhead lettuce type)
↓ resistant* BC1 plant X *L. sativa* (butterhead lettuce type)

↓ resistant* BC2 plant X *L. sativa* (butterhead lettuce type)

↓ resistant* BC3 plant self-pollination

The BC3Z population was tested and markers D1 and D2 identified. The individual BC3Z plants were self-pollinated and from the BC3Z2 populations the individual BC3Z2 plants homozygous for gene D were selected and used for linking analysis of the diverse identified DNA-markers (Example 3).

Example 3

Linking Analysis of the Identified DNA-markers

There are different methods of demonstrating whether diverse qualitative resistance genes can be positioned in the same or in different linking groups (chromosomes).

A. Genetic Map

Determining of the position of DNA-markers can be carried out by generating a genetic map of the 9 chromosomes of lettuce. In order to generate a genetic map on which the position of the diverse molecular DNA-markers is indicated, crossings are made between lettuce plants which are highly polymorphic relative each other from a genetic viewpoint. For this type of crossing with a high degree of polymorphism a distinction can be made between:

intraspecific crossing:

This is a crossing between for instance butterhead lettuce and iceberg lettuce, a crossing is made within a species (*L.sativa*), interspecific crossing:

This is a crossing between two *Lactuca* species, for instance butterhead lettuce (*L.sativa*) with *L.virosa*.

An F2 or BC1 population is generated of both types of crossing. By analysing this F2 or BC1 population with for instance RAPD-markers all plants can be individually analysed for the presence or absence of the polymorphic molecular DNA-markers. By analysing the obtained data using a computer program such as for instance JoinMap (Stam, Plant Journal 3, 739–744, 1993), linking groups can be constructed which place the diverse tested DNA-markers linearly relative to each other, separated by specific recombination distances denoted in centiMorgans. If a broad-spectrum Dm-resistance gene segregates in the used F2 or BC1 population, the broad-spectrum Dm-resistance gene can, after testing with *B.lactucae*, be placed within one of the linking groups shown on a detailed genetic map of lettuce. A genetic lettuce map with 9 linking groups has been described by Michelmore (Genetics 116, 331–337, 1987).

When the identified molecular DNA markers according to the present invention are polymorphic in the parents used to make an F2 or BC1 population, these DNA-markers can be placed on the genetic map, whereby it is possible to establish whether the DNA-markers originate from the same or from different linking groups, B. Test Crossings Another method for determining the position of the DNA-markers as applied in the present invention linked to the resistance genes consists of studying the dependent or independent segregation of the different DNA-markers. Selected for this purpose from the four populations were individual plants which are homozygous for the specific broad spectrum Dm-resistance genes from respectively population A, B, C or D. Specific crossings were then made for the generation of a segregating F2 population in which all Dm-resistance genes and their corresponding DNA-markers were present.

Selection of Plant with Gene A and B

A plant homozygous for Dm-resistance gene A (as demonstrated with marker A) was crossed with a plant homozygous for Dm-resistance gene B (marker B). The individual F1 plant with both Dm-resistance gene A and B (after analysis with the DNA-markers A and B), as well as the individual plants of the F2 population were subsequently self-pollinated. A selection was made from the F3 populations of plants which were homozygous for both Dm-resistance gene A and for Dm-resistance gene B, using the DNA-markers specific for Dm-resistance gene A and B.

Being able to select a plant with the qualitative Dm-resistance genes A and B each having a broad-spectrum Dm-resistance means that both resistance genes are localized in different linking groups.

Selection of a Plant with Both Genes C and D

A plant homozygous for Dm-resistance gene C (as demonstrated with markers C1, C2, C3 or C4) was crossed with a plant homozygous for Dm-resistance gene D (markers D1 or D2). The individual F1 plant with both Dm-resistance gene C and D (after analysis with the DNA-markers C1, C2, C3 or C4 and D1 or D2), as well as the individual plants of the F2 population were subsequently self-pollinated. A selection was made from the F3 populations of plants which were homozygous for Dm-resistance gene C and for Dm-resistance gene D, using the DNA-markers specific for the Dm-resistance genes C and D.

Being able to select a plant with the qualitative Dm-resistance genes C and D each having a broad-spectrum Dm-resistance means that both resistance genes are localized in different linking groups.

Example 4

Linking Analysis for the 4 Genes from the 4 Different Populations

The selected plant homozygous for Dm-resistance genes A and B was then crossed with the selected plant homozygoqs for Dm-resistance genes C and D. The F1 plants heterozygous for the Dm-resistance genes A, B, C and D (as determined with the DNA-markers specific to these genes) were self-pollinated.

The F2 population was tested in the *B.lactucae* disease test and analysed with the DNA-markers for the 4 broad-spectrum Dm-resistance genes.

For the disease test three to six leaf punches with a cross-section of 18 to 20 mm were taken from lettuce plants for testing with a cork drill, or 50 seeds were laid out on a filter paper. The punches or filter papers with lettuce seed were laid in a tray on wet thick filter paper and covered with a glass plate until the moment of inoculation. The punches were inoculated on the same day or a few days after the punching. The seeds were germinated and further cultivated in a climate cell of 12–16° C. with 16 hours of light and 8 hours of darkness until the seed leaves were extended, whereafter inoculation took place.

The *B.lactucae* inoculum was prepared by arranging a determined physio of *B.lactucae*, (fresh or frozen) which sporulates on leaf material, in a small measured quantity of water, mixing it and sieving this solution. The concentration of living spores was then determined by means of fluorescence microscopy and adjusted if necessary. The optimal spore concentration is 10,000–50,000 virulent spores/ml water.

The inoculum was applied to the punches or seedlings with a plant spray until the punches were slightly moist. The tray was then covered again with a glass plate and set aside at 12–16° C. and 16 hours light and 8 hours of darkness. After 10 to 14 days it was possible to assess the punches for the degree of development and sporulation and it was possible to state whether a tested plant or lettuce number is resistant or susceptible to the tested B.lactucae physio.

The DNA-marker analysis was performed as described in Example 1.

Of the made F2 population, 24 plants are shown in table 1 and FIGS. 7–14 which were tested in the B.lactucae disease test and analysed with the RAPD-markers. From this test it was found that the eight RAPD-markers can be split independently of each other and can therefore be positioned in four different linking groups.

Conclusion

FIGS. 7–14 show that the DNA-markers linked to the 4 broad-spectrum Dm-resistance genes segregate independently of each other and can thus be positioned in the four separate linking groups. Plants can hereby be selected which comprise at least 2, preferably 3, and most preferably 4 qualitative resistance genes (indicated with: * in table 1 below), have a broad-spectrum Dm-resistance and are therefore valuable for processing to a commercial lettuce variety.

Only application of the DNA-markers according to the invention makes such a selection possible because in the B.lactucae disease test no distinction can be made between the presence of one or more qualitative broad-spectrum Dm-resistance genes.

Corresponding results were obtained with the other wild lettuce species.

TABLE 1

RAPD-markers originating from 4 different linkage groups (chromosomes).

| F2 plant No. | Disedoe test | Marker A | Marker B | Marker C1 | Marker C2 | Marker C3 | Marker C4 | Marker D1 | Marker D2 | Plants with all markers(*) |
|---|---|---|---|---|---|---|---|---|---|---|
| 1 | R | + | + | − | − | − | − | + | + | |
| 2 | R | − | + | − | − | − | − | − | − | |
| 3 | R | − | − | + | + | + | + | + | + | |
| 4 | R | + | + | + | + | + | + | + | + | + |
| 5 | R | + | − | + | + | + | + | + | + | |
| 6 | R | + | + | + | + | + | + | − | − | |
| 7 | R | + | + | − | − | − | − | − | − | |
| 8 | R | + | + | + | + | + | + | + | + | + |
| 9 | R | + | − | + | + | + | + | + | + | |
| 10 | R | + | + | + | + | + | + | + | + | |
| 11 | R | + | + | − | − | − | − | + | + | |
| 12 | R | + | + | + | + | + | + | − | − | |
| 13 | R | + | + | − | − | − | − | + | + | |
| 14 | R | + | + | − | − | − | − | + | + | |
| 15 | R | + | − | + | + | + | + | − | − | |
| 16 | R | + | + | + | + | + | + | + | + | + |
| 17 | R | + | − | + | + | + | + | − | − | |
| 18 | R | + | + | + | + | + | + | + | + | + |
| 19 | R | − | − | − | − | − | − | + | + | |
| 20 | R | + | − | + | + | + | + | + | + | |
| 21 | R | − | − | + | + | + | + | + | + | |
| 22 | R | + | − | + | + | + | + | − | − | |
| 23 | R | + | + | + | + | + | + | + | + | + |
| 24 | R | + | + | + | + | + | + | + | + | + |

R = resistant
Marker A = OPAF06/451 bp
Marker B = OPAM10/565 bp
Marker C1 = OPW16/750 bp
Marker C2 = OPL03/276 bp
Marker C3 = OPAE19/675 bp
Marker C4 = UBC711/1083 bp
Marker D1 = OPW04/520 bp
Marker D2 = OPW19/963 bp

What is claimed is:

1. A lettuce plant with a lasting resistance to *Bremia Iactucae*, wherein the lettuce plant is produced from a cultivated lettuce plant (*L. sativa*) crossed with a wild lettuce plant having at least one broad-spectrum Dm-resistance gene and further wherein said wild lettuce plant is represented by an accession number selected from the group consisting of CGN9365, CGN4683, CGN5148 and CGN5913.

2. The lettuce plant as claimed in claim 1, wherein the cultivated lettuce plant is selected from the group consisting of head lettuce (*L. sativa Lineaus capitata*); leaf lettuce for picking (*L. sativa Lineaus acephala*); cos lettuce (*L. sativa Lineaus romana*); leaf lettuce for cutting (*L. sativa Lineaus secalina*) and asparagus lettuce (*L. sativa Lineaus angustana*).

3. The lettuce plant as claimed in claim 2, wherein the cultivated lettuce plant is selected from the group consisting of iceberg lettuce, batavia lettuce and butterhead lettuce.

4. The lettuce plant as claimed in claim 2, wherein the cultivated lettuce plant is selected from the group consisting of curly leaf lettuce and stem lettuce.

5. The lettuce plant as claimed in claim 1, wherein the plant's chromosomes comprise comprises a DNA-sequence selected from the group consisting of (SEQ ID NO: 1), (SEQ ID NO: 2), (SEQ ID NO: 3), (SEQ ID NO: 4), (SEQ ID NO: 5) and (SEQ ID NO: 6).

6. A seed of the lettuce plant as claimed in claim 1.

* * * * *

UNITED STATES PATENT AND TRADEMARK OFFICE
CERTIFICATE OF CORRECTION

PATENT NO. : 6,903,249 B2 Page 1 of 1
APPLICATION NO. : 09/959037
DATED : June 7, 2005
INVENTOR(S) : Lambalk et al.

It is certified that error appears in the above-identified patent and that said Letters Patent is hereby corrected as shown below:

Column 17, Line 40, Claim 1, "*Iactucae*" should read -- *lactucae* --

Column 18, Line 46, Claim 5, "comprise comprises" should read -- comprise --.

Signed and Sealed this

Eighth Day of August, 2006

JON W. DUDAS
*Director of the United States Patent and Trademark Office*

SEQUENCE LISTING

<160> NUMBER OF SEQ ID NOS: 6

<210> SEQ ID NO 1
<211> LENGTH: 451
<212> TYPE: DNA
<213> ORGANISM: Lactuca virosa
<220> FEATURE:
<223> OTHER INFORMATION: DNA Marker A

<400> SEQUENCE: 1

```
ccgcagtctg agttgagcaa tcgatggata gttgagtcgt tacttttttgt ggcaagagtt    60 gcattgttcc cgttcctggg aaaagcgaag taactatcga aattccggtt tcaaagtttg   120
gaggtaggct ccgtagggta gcattgatgg tgacccttttt catcagagta tttgggcagt   180
ttgtatgctg taaggtattt tcttttacca tggagtcatt ggtggaggat gagatggaag   240
agatccatga aggtgccttt tgaggatggc atgcatttag cagcggtttc aggtagtaag   300
aggaatatat cagggcggtg gccctcatag ttaggattgt gcatcggtta tgagagtgag   360
accttgtgtc ttgatgatga ttcccgtgtt gggaggcggg tcgatgaatc aaagacgagg   420
ggtgtgatag tgtattattt ccagactgcg g                                  451
```

<210> SEQ ID NO 2
<211> LENGTH: 555
<212> TYPE: DNA
<213> ORGANISM: Lactuca virosa
<220> FEATURE:
<223> OTHER INFORMATION: DNA Marker B

<400> SEQUENCE: 2

```
cagaccgacc caacccttttc gacttccgat ttctaacggt tcttttttata aaacattcct    60 aaattaccat actaacaaaa taacatttcc atttatctta agccccttaa cttttgtttt   120
tttactttaa cctgccttttt ttcttttttaa tttttattac aaatttagtc taaacttatt   180 tttttttacaa ctttcttttt atataatttc taaaatttag gcttttaaaa aaaattattt   240
tgttacaatt ttataaaatt tgatttttta caaatattct tttaatttg ttttatattt   300 tcttttctta gattttttctg atttttataaa ttatatttttt ttaattagtt ttctatattc   360
tacaaaaatt attttttaca taatttttttt ttcaaattgt tttaaaaaaa ctaatattct   420
ttagaaaatt attttttacaa agagttatat atttggttttt atgcatgtat ttttaaaaaaa   480 ttcccgcatt taaataaata ttattcttta aatttatttt actatttttta tatattcatt   540 tacatggtcg gtctg                                                    555
```

<210> SEQ ID NO 3
<211> LENGTH: 276
<212> TYPE: DNA
<213> ORGANISM: Lactuca virosa
<220> FEATURE:
<223> OTHER INFORMATION: DNA Marker C2

<400> SEQUENCE: 3

```
ccagcagctt gccaaacaaa ggctaaaaga aaaagaaaca ggggtatgac tggcataaca    60
tctacgattg gattcaaaaa agcataggct tcgggcaatt tagcgaagaa aagactactt   120
ggataaaggg tagaattaag acagatcaaa gtaaagatat tatgcataac atacatttttg   180 ttcgtcgaga taattgcatt ttgattgagt taggaagaga attcaatgtt tgaagaatga   240
attgtctaaa acaattgttg gattcgaagc tgctgg                             276
```

<210> SEQ ID NO 4
<211> LENGTH: 675
<212> TYPE: DNA
<213> ORGANISM: Lactuca virosa
<220> FEATURE:
<223> OTHER INFORMATION: DNA Marker C3

<400> SEQUENCE: 4

```
gacagtccct tcactagtac ttgctttact aaaacaacac aactataatc catcttaatt    60
```

-continued

| | |
|---|---|
| tccttctacg tacagattaa taagcaaaat gaattgaact tttttggcaa cttaaatttc | 120 |
| gagtccctac actagtactt gatagatcta ctttcatttt ctcccacccc catgtggtca | 180 |
| atcgcttgtt aaggtgacat ataaaaccac tctctaaagt catccttctt aatgtcatca | 240 |
| cctaagaggc ttatttcttc ctcttttcca gtaaacataa acaagaacat gtgatataat | 300 |
| gaaacaaaaa tagaaatttc aactgttaaa aagaattgat tctgtaacac cctgtttatt | 360 |
| tattagataa ataaattaat tactgaacaa atggtagccc taaataaat aattatatat | 420 |
| caaaggatgg tctcgaggaa ctaattgtca caagtttcga agttggggt taaaagtgtg | 480 |
| agtttcggat tgattttgta aatatttgtg gaggcaagga ctaaatagta aattattgac | 540 |
| ttcatttgaa aataaatgta ggaggagggg ctacttggta aagttggac ttaattagta | 600 |
| agggatttaa gaggcagggt tcaactggta ccttatgggt tcactttgaa agaagaatgg | 660 |
| tatggaggga ctgtc | 675 |

<210> SEQ ID NO 5
<211> LENGTH: 1083
<212> TYPE: DNA
<213> ORGANISM: Lactuca virosa
<220> FEATURE:
<221> NAME/KEY: variation
<222> LOCATION: 788
<223> OTHER INFORMATION: Variation
<223> OTHER INFORMATION: DNA Marker C4

<400> SEQUENCE: 5

| | |
|---|---|
| gggagaggga gatactatgt ttgtttctcg cgtatcaaag attactccgt taagggtaat | 60 |
| attaattcca gtacttctcg tcaagtcaac tttaaacact tgtaccacag cgttaggaaa | 120 |
| aatctgaacg aaccttgtta ctatcctcca aagaaaaacc aaaaacccct ccttattttc | 180 |
| acgagcatac caacaatcta tttccccaac tttccccagc tttcctacga tgttgacact | 240 |
| acatattgaa caagaacata agtactacaa tccattctgt cgcctgcgcc gtaacaatgc | 300 |
| cttaactgcc aagtagaacc tcttggtaaa aacagaaccc tgaaggacta atataactag | 360 |
| cgaagaggtt aggaagtact agtgacgcta tccgactttt atagttagta attatttgtg | 420 |
| aatatttcct attaattggg tgatcttcta attgaaacta tctgtagtat tttgcgactg | 480 |
| gcgtttacaa ttaagatttt ttcaattaat ccatactaac aactatactt ttaraactac | 540 |
| atatarttat tkcccttacc gaagccttat tccgtgtagt tttaaaagaa gtatctttgt | 600 |
| agttatagtt gctacatatg ttcaagtcc agagatttag ctggtggtat tgtgtttgtt | 660 |
| aagttcgtca aattccaata gtaccctac ccatatgttg aattgatatg agtggttaaa | 720 |
| gaaatctctg aaagactcgg gacctttaag tcaagggaag gagttgcgtt caaaacagta | 780 |
| gggacatnta aatccttcta aatgtgaact ccaccgcttg atgggaaaaa aaaaaaaaaa | 840 |
| agactttcc ctttagatta ttttactttt ctcgactta cctaaatatc cagacctcca | 900 |
| atgtactttg atattatatg tacaaacgat tgttcaacag aatatattc attagtagtt | 960 |
| gttcgatgta gattcgcttt tctttgacgt tattgcttaa tgtttttact actccatcta | 1020 |
| ttgtttaatc tttcactgtc tcatatgaaa cttctattcc ttaagttctc ccctccctct | 1080 |
| ccc | 1083 |

<210> SEQ ID NO 6
<211> LENGTH: 963
<212> TYPE: DNA
<213> ORGANISM: Lactuca virosa
<220> FEATURE:

-continued

```
<221> NAME/KEY: variation
<222> LOCATION: 808
<223> OTHER INFORMATION: Variation
<223> OTHER INFORMATION: DNA Marker D2

<400> SEQUENCE: 6
caaagcgctc catcttgtag gattcttttta ttggtaggaa atgggcggat ttcgttagtc      60
tatcaactat tacccagatt gtgtccaaac tgtctggcga cttgggtagt ttgatcacga     120
aatccatggt aatcctttcc catttccact cgggaattac tagctgctgt agtaatccag     180
agggcttctg atatttaacc tttactttag cacaagtgag gcacttgctt acgtaagtgt     240
aatctctgcc ttcatatttg gccaccaata atgctgctta acatctaagt acatcttgtc     300
tgaacccgga tggatggagt atcgcgtctt gtgagcctcg ttcatgaata cctctctgaa     360
ttccccaagt ttagggacca atatgcggtt catgaagtag tatgttccat cttccttcac     420
ctccaagttc ttctccattc cacgcagcgc ttcactcgtt ttgttctccg ccttcatggc     480
atctgactga gtcgttctga tttgcgaggt tagatgggat tggatggtta tcgagagagt     540
tttcatacaa agacttgagt attctttctg actcaaggca tcggctacca cgttagcctt     600
gcctggatgg tacttgatgt cgcactcata gtcgttcagc agttcgaccc atcttcattg     660
cctcatgttt agctcctttt gattcaagat gtgctgaaga ctcttgttgt cagtgaagat     720
agtgcacttg gtaccgtata ggtagtgtct ccagattttc agggcgaaga ccactgcacc     780
cagttccaga tcgtgggtcg tataattnct tcgtgtgtct ttagctgtcg ggacgcgtaa     840
gctatcaccc ttccacgctg catgagtaca cagcctaaac cctgatttga cgcatcgcag     900
tagactataa agtcttctgt tccttcaggt agtgatagca ccggtgcact gcagagcgct     960
ttg                                                                    963
```